(12) United States Patent
Cawthern et al.

(10) Patent No.: US 11,460,477 B2
(45) Date of Patent: *Oct. 4, 2022

(54) TWO COMPONENT "MIX AND USE" LIQUID THROMBOPLASTIN REAGENT, METHODS OF MAKING, AND METHODS OF USE THEREOF

(71) Applicant: Instrumentation Laboratory Company, Bedford, MA (US)

(72) Inventors: Kevin M. Cawthern, Cornwall On Hudson, NY (US); Ralph E. Bottenus, Hillsborough, NJ (US); Chun Kung, Nanuet, NY (US)

(73) Assignee: INSTRUMENTATION LABORATORY COMPANY, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/098,740

(22) Filed: Nov. 16, 2020

(65) Prior Publication Data

US 2021/0080476 A1 Mar. 18, 2021

Related U.S. Application Data

(63) Continuation of application No. 15/429,480, filed on Feb. 10, 2017, now Pat. No. 10,877,052.

(60) Provisional application No. 62/294,367, filed on Feb. 12, 2016.

(51) Int. Cl.
*G01N 33/86* (2006.01)

(52) U.S. Cl.
CPC ..... *G01N 33/86* (2013.01); *G01N 2333/7454* (2013.01); *G01N 2333/96463* (2013.01)

(58) Field of Classification Search
CPC .......... G01N 33/86; G01N 2333/7454; G01N 2333/96463
USPC ........................................................ 435/13
See application file for complete search history.

(56) References Cited

U.S. PATENT DOCUMENTS

| 5,314,695 | A | 5/1994 | Brown |
| 5,508,170 | A | 4/1996 | Butler et al. |
| 6,733,985 | B1 | 5/2004 | Lee |
| 8,617,834 | B2 | 12/2013 | Rechner |
| 2009/0061468 | A1 | 3/2009 | Hoshiko et al. |

FOREIGN PATENT DOCUMENTS

| CA | 2265270 | 11/2009 |
| EP | 1536236 | 6/2005 |
| EP | 1536236 | 8/2005 |
| EP | 2031402 | 3/2009 |
| EP | 2031402 A1 | 3/2009 |
| JP | H11160320 | 6/1999 |
| JP | H11160320 A | 6/1999 |
| JP | 2002526557 | 8/2002 |
| JP | 2002526557 A | 8/2002 |
| JP | 2009058393 | 3/2009 |
| WO | 2002052276 | 7/2002 |
| WO | 20002052276 | 7/2002 |
| WO | 2017139567 A1 | 8/2017 |

OTHER PUBLICATIONS

International Preliminary Report on Patentability in corresponding PCT Application No. PCT/US17/017360, dated Aug. 23, 2018 (7 pages).
Office Action from corresponding Japanese Application No. 2018-540156, dated Aug. 21, 2019 and English translation thereof (9 pages).
First Examination Report from corresponding Australian Application No. 2017-217804, dated Oct. 14, 2019 (4 pages).
First Office Action issued in counterpart Chinese Patent Application No. 201780011858, dated Apr. 24, 2020 and English translation thereof (8 pages).
Second Examination Report from corresponding Australian Patent Application No. 2017217804, dated Jul. 23, 2020 (3 pages).
Third Examination Report from corresponding Australian Patent Application No. 2017217804, dated Sep. 29, 2020 (3 pages).
Second Office Action from corresponding Chinese Patent Application No. 201780011858, dated Sep. 22, 2020, and English translation thereof (17 pages).
Third Office Action from corresponding Chinese Patent Application No. 201780011858, dated Mar. 11, 2021, and English translation thereof (10 pages).
Communication Pursuant to Article 94(3) EPC for European patent application No. 17707447.3, dated Jun. 4, 2021, (5 pages).
Third Examination Report issued in counterpart Australian patent application No. 2017217804 dated Sep. 29, 2020, 3 pages.
Second Office Action issued in counterpart Chinese patent application No. 2017800111858 dated Sep. 22, 2020, 9 pages and English summary thereof, 8 pages.
Second Examination Report in counterpart Australian patent application No. 2017217804 dated Jul. 23, 2020, 3 pages.
English summary of Office Action issued in counterpart Chinese patent application No. 2017800111858 dated Apr. 24, 2020, 8 pages.
First Office Action Issued in counterpart Chinese patent application No. 2017800111858 dated Apr. 24, 2020, 8 pages.
Examiner Requisition with accompanying Examination Search Report issued in counterpart Canadian patent application No. 3013356 dated Nov. 5, 2019, 4 pages.
Australian Patent Office, Examination Report No. 1, issued in corresponding Australian application No. 2017217804, dated Oct. 14, 2019, 4 pages.
Office Action from related Japanese Application No. 2018-540156, dated Aug. 21, 2019 and English translation thereof, 9 pages.
International Preliminary Report on Patentability from related Application No. PCT/US17/17360, dated Aug. 23, 2018, 7 pages.
International Search Report and Written Opinion In corresponding PCT Application No. PCT/US2017/017360 dated Apr. 19, 2017. (10 Pages).

*Primary Examiner* — Jennifer M. H. Tichy
(74) *Attorney, Agent, or Firm* — Burns & Levinson LLP

(57) ABSTRACT

What is described is a kit for preparing a liquid thromboplastin reagent for a prothrombin time assay. The kit simplifies and minimizes reagent preparation time and is stable for 2-5 years.

28 Claims, 9 Drawing Sheets

Table 1: Real Time Stability Results for Lot 1 (RD790608)

| PT: Two component mix and use liquid thromboplastin Lot 1 Stability With Original Control (no crossover) ||| | | | | | | | Spec. |
|---|---|---|---|---|---|---|---|---|---|---|---|
| Lot 1 | PT | | Time Points (Month) ||||||| |
| | | | 0 | 5 | 12 | 15 | 18 | 24 | 30 | 55 | |
| NC | PT (Sec) | Mean | 11.4 | 11.4 | 11.6 | 11.6 | 11.8 | 11.9 | 11.9 | 12.3 | |
| | | Δ % | 0 | 0 | 1.8 | 1.8 | 3.5 | 4.4 | 4.4 | 7.9 | ≤10% |
| Low Ab Con | PT (Sec) | Mean | 19.7 | 20.1 | 20.3 | 20.0 | 20.3 | 20.2 | 19.6 | 19.7 | |
| | | Δ % | 0 | 2.0 | 3.0 | 1.5 | 3.0 | 2.5 | -0.5 | 0 | ≤15% |
| High Abn | PT (Sec) | Mean | 37.3 | 37.4 | 37.6 | 37.3 | 37.8 | 37.5 | 36.1 | 35.6 | |
| | | Δ % | 0 | 0.3 | 0.8 | 0 | 1.3 | 0.5 | -3.2 | -4.6 | ≤15% |

| dFib: Two component mix and use liquid thromboplastin Lot 1 Stability With Original Control (no crossover) ||| | | | | | | | Spec. |
|---|---|---|---|---|---|---|---|---|---|---|---|
| Lot 1 | dFib | | Time Points (Month) ||||||| |
| | | | 0 | 5 | 12 | 15 | 18 | 24 | 30 | 55 | |
| NC | dFib | Mean | 287 | 290 | 290 | 270 | 285 | 284 | 283 | 281 | |
| | (mg/dL) | Δ % | 0 | 1.0 | 1.0 | -5.9 | -0.7 | -1.0 | -1.4 | -2.1 | ≤15% |
| Low Ab Con | dFib | Mean | 142 | 137 | 150 | 145 | 147 | 145 | 155 | 156 | |
| | (mg/dL) | Δ % | 0 | -3.5 | 5.6 | 2.1 | 3.5 | 2.1 | 9.2 | 9.9 | ≤15% |
| Low Fib Con | dFib | Mean | 128 | 129 | 146 | 144 | 146 | ND | ND | 154 | |
| | (mg/dL) | Δ % | 0 | 0.8 | 14.1 | 12.5 | 14.1 | ND | ND | 20 | ≤15% |

NC- Normal Control plasma
low Ab Con = Low Abnormal Control plasma
High Abn = High Abnormal Control plasma
dFib = Derived Fibrinogen value

FIG. 1A

Table 2: Real Time Stability Results for Lot 2 (RD791108)

| PT: Two component mix and use liquid thromboplastin Lot 2 Real Time Stability With Original Control (no crossover) | | | | | | | | | Spec. |
|---|---|---|---|---|---|---|---|---|---|
| Lot 2 | PT | | Time Points (Month) | | | | | | |
| | | | 0 | 3 | 6 | 9 | 12 | 18 | 43 | |
| NC | PT (Sec) | Mean | 11.6 | 11.8 | 11.6 | 12.1 | 12.1 | 11.6 | 12.8 | |
| | | Δ% | 0 | 1.7 | 0 | 4.3 | 4.3 | 0 | 10.3 | ≤10% |
| Low Ab Con | PT (Sec) | Mean | 22.5 | 22.8 | 22.4 | 23.0 | 23.4 | 22.4 | 23.3 | |
| | | Δ% | 0 | 1.3 | -0.4 | 2.2 | 4.0 | -0.4 | 3.6 | ≤15% |
| High Abn | PT (Sec) | Mean | 37.2 | 37.7 | 36.9 | 38.0 | 38.9 | 37.2 | 38.4 | |
| | | Δ% | 0 | 1.3 | -0.8 | 2.2 | 4.5 | 0 | 3.2 | ≤15% |

| dFib: Two component mix and use liquid thromboplastin Lot 2 Real Time Stability With Original Control (no crossover) | | | | | | | | | Spec. |
|---|---|---|---|---|---|---|---|---|---|
| Lot 2 | dFib | | Time Points (Month) | | | | | | |
| | | | 0 | 3 | 6 | 9 | 12 | 18 | 43 | |
| NC | dFib | Mean | 334 | 334 | 330 | 371 | 333 | 338 | 316 | |
| | (mg/dL) | Δ% | 0 | 0 | -1.2 | 11.1 | -0.3 | 1.2 | -5.4 | ≤15% |
| Low Ab Con | dFib | Mean | 161 | 167 | 170 | 182 | 166 | 173 | 172 | |
| | (mg/dL) | Δ% | 0 | 3.7 | 5.6 | 13.0 | 3.1 | 7.5 | 6.8 | ≤15% |
| Low Fib Con | dFib | Mean | 136 | 145 | 144 | 155 | 143 | 148 | 155 | |
| | (mg/dL) | Δ% | 0 | 6.6 | 5.9 | 14.0 | 5.1 | 8.8 | 14.0 | ≤15% |

FIG. 1B

Table 3: Real Time Stability Results for Lot 3 (N1290895)

| PT: Two component mix and use liquid thromboplastin Lot 3 Real Time Stability With Original Control (no crossover) | | | | | | | | | Spec. |
|---|---|---|---|---|---|---|---|---|---|
| Lot 3 | PT | | Time Points (Month) | | | | | | |
| | | | 0 | 3 | 6 | 9 | 12 | 15 | 38 | |
| NC | PT (Sec) | Mean | 11.5 | 11.5 | 11.7 | 11.4 | 11.7 | 11.9 | 12.0 | |
| | | Δ % | 0 | 0 | 1.7 | -0.9 | 1.7 | 3.5 | 4.3 | ≤10% |
| Low Ab Con | PT (Sec) | Mean | 21.3 | 19.3 | 20.5 | 20.6 | 21.6 | 21.3 | 21.7 | |
| | | Δ % | 0 | -9.4 | -3.8 | -3.3 | 1.4 | 0 | 1.9 | ≤15% |
| High Abn | PT (Sec) | Mean | 35.3 | 31.4 | 31.4 | 33.2 | 35.5 | 34.7 | 34.6 | |
| | | Δ % | 0 | -11.1 | -11.1 | -5.9 | 0.6 | -1.7 | -2.0 | ≤15% |

| dFib: Two component mix and use liquid thromboplastin Lot 3 Real Time Stability With Original Control (no crossover) | | | | | | | | | Spec. |
|---|---|---|---|---|---|---|---|---|---|
| Lot 3 | dFib | | Time Points (Month) | | | | | | |
| | | | 0 | 3 | 6 | 9 | 12 | 15 | 38 | |
| NC | dFib | Mean | 298 | 316 | 308 | 298 | 303 | 311 | 309 | |
| | (mg/dL) | Δ % | 0 | 6.0 | 3.4 | 0 | 1.7 | 4.4 | 3.7 | ≤15% |
| Low Ab Con | dFib | Mean | 123 | 127 | 130 | 121 | 121 | 128 | 122 | |
| | (mg/dL) | Δ % | 0 | 3.3 | 5.7 | -1.6 | -1.6 | 4.1 | -0.8 | ≤15% |
| Low Fib Con | dFib | Mean | 136 | 145 | 137 | 135 | 134 | 142 | 149 | |
| | (mg/dL) | Δ % | 0 | 6.6 | 0.7 | -0.7 | -1.5 | 4.4 | 9.6 | ≤15% |

FIG. 1C

TABLE 4

| | PTRDP1 | PTRDP2 | PTRDP3 | PTRDP4 | PTRDP5 | PTRDP6 |
|---|---|---|---|---|---|---|
| UNTREATED P4 POST STRESS 37°C | S | S | S | S | S | S |
| NORMAL CTL | FAILED | 10.4 | 297.2 | 235.5 | FAILED | FAILED |
| | FAILED | 316.5 | 306.0 | 241.9 | FAILED | FAILED |
| | FAILED | FAILED | 310.8 | 242.0 | FAILED | FAILED |
| | FAILED | FAILED | 311.9 | 236.3 | FAILED | FAILED |
| LOW ABN | FAILED | FAILED | FAILED | FAILED | FAILED | FAILED |
| | FAILED | FAILED | 8.1 | FAILED | FAILED | FAILED |
| | FAILED | FAILED | FAILED | FAILED | FAILED | FAILED |
| | FAILED | FAILED | FAILED | FAILED | FAILED | FAILED |
| HIGH ABN | FAILED | FAILED | FAILED | FAILED | FAILED | FAILED |
| | FAILED | FAILED | FAILED | FAILED | FAILED | FAILED |
| | FAILED | FAILED | FAILED | FAILED | FAILED | FAILED |
| | FAILED | FAILED | FAILED | FAILED | FAILED | FAILED |
| | PTRDP1 | PTRDP2 | PTRDP3 | PTRDP4 | PTRDP5 | PTRDP6 |
| 1mM EDTA-TREATED P4 POST STRESS 37°C | S | S | S | S | S | S |
| NORMAL CTL | 11.0 | 11.4 | 11.1 | 11.4 | 11.1 | 11.4 |
| | 11.3 | 11.2 | 11.2 | 11.2 | 11.2 | 11.3 |
| | 11.4 | 11.4 | 11.3 | 11.4 | 11.3 | 11.3 |
| | 11.4 | 11.3 | 11.5 | 11.1 | 11.4 | 11.1 |
| LOW ABN | 22.2 | 22.7 | 21.9 | 22.6 | 21.5 | 22.5 |
| | 22.4 | 22.3 | 22.5 | 22.5 | 22.4 | 22.2 |
| | 22.5 | 22.7 | 22.6 | 22.4 | 22.1 | 22.3 |
| | 22.7 | 21.6 | 22.3 | 21.8 | 22.3 | 21.0 |
| HIGH ABN | 37.6 | 38.3 | 36.0 | 38.3 | 36.1 | 37.7 |
| | 37.6 | 37.4 | 38.1 | 38.1 | 37.5 | 37.6 |
| | 37.6 | 37.7 | 37.0 | 38.1 | 37.9 | 37.6 |
| | 37.5 | 35.6 | 37.5 | 36.3 | 37.9 | 36.6 |

FIG. 3

TWO COMPONENT "MIX AND USE" LIQUID THROMBOPLASTIN REAGENT, METHODS OF MAKING, AND METHODS OF USE THEREOF

CROSS-REFERENCE TO RELATED APPLICATIONS

This application is a continuation of, and claims priority to, U.S. patent application Ser. No. 15/429,480, which was filed on Feb. 10, 2017. U.S. patent application Ser. No. 15/429,480 is incorporated herein by reference. This application also claims the benefit of U.S. Provisional Application No. 62/294,367, filed Feb. 12, 2016, the entire disclosure of which is herein incorporated by reference.

FIELD OF THE INVENTION

The field of the invention is related to reagents for preparing an assay for assessing coagulation in a patient, more specifically reagents for prothrombin time assays, kits for coagulation assays, and methods of preparing such assays.

BACKGROUND OF THE INVENTION

The prothrombin time (PT) is used with patient plasmas to determine either naturally occurring deficiencies in the extrinsic pathway of blood coagulation, or those induced by the prescription of oral vitamin K antagonists (VKAs) such as coumadins. The PT is routinely performed in the clinical setting using a manual or automated test method that mixes a working thromboplastin solution with human patient plasma collected in a stabilizing amount of chelator (e.g., citrate). Working thromboplastin solutions are comprised minimally of tissue factor (natural (TF) or recombinant (rTF)) in complex with a pro-coagulant lipid membrane surface, and calcium ions as a requisite cofactor to replace those that were chelated in the plasma when blood was drawn from a patient to prevent clotting. Working thromboplastin solutions are presented in either liquid or freeze dried form.

Currently available liquid thromboplastins include all of the components in a single vial; this is disadvantageous because of limitations in long term stability and shelf life which is no greater than 1 year when maintained at 2-8° C. Additionally, currently available freeze-dried thromboplastins are disadvantageous because they require significant preparation time for reconstitution before use and introduce additional variability in precision of the PT measurement through the reconstitution process.

SUMMARY OF THE INVENTION

In one aspect, the invention is directed to a kit for preparing a liquid thromboplastin reagent for measuring prothrombin time in a patient. In one embodiment, the kit includes a first container and a second container. The first container contains a coagulation factor III (tissue factor, CD142) combined with a lipid mixture and a chelator. The chelators may be, for example, but not limited to citrate, EDTA, EGTA, nitrilotriacetic acid (NTA), ethylene diamine, N-(2-Acetamido)iminodiacetic acid (ADA), tartrate, glycinate, BAPTA, oxalate, phosphate, diphosphate, polyphosphate, organic phosphonates, and combinations thereof. The concentration of the chelator is greater than about 0 mM to about 100 mM, greater than about 0 to about 50 mM, greater than about 0 mM to about 25 mM, about 10 mM to about 50 mM, for example, and for EDTA, about 0.5 mM and for citrate, about 11 mM, for example. The lipid mixture includes phospholipids, cholesterol, fatty acids, sphingolipids, mono-glycerides, di-glycerides, tri-glycerides, extracts of naturally occurring lipids and combinations thereof, for example. The source of coagulation factor III (tissue factor) includes but is not limited to a recombinant tissue factor or a native tissue factor extracted from brain or other tissue.

The second container in this embodiment of the invention includes a calcium solution, typically in a buffer at a concentration ranging from about 5 mM to about 500 mM, about 5 mM to about 100 mM, about 10 mM to about 75 mM, about 25 mM to about 50 mM, about 5 mM to about 25 mM, and about 9 mM to about 15.5 mM, for example.

The kit according to this embodiment of the invention has a shelf-life of at least 2 to 5 years.

In another embodiment of this aspect of the invention, the kit has all of the same features as the kit described above with the exception of a chelator.

In another aspect, the invention is directed to a method for preparing a liquid thromboplastin reagent for measuring prothrombin time in a patient. In one embodiment of the method of the invention, the first step of the method provides coagulation factor III (tissue factor) as described above in the ranges described above, a lipid mixture from the sources described above, and a chelator from the group described above in the concentration ranges described above. In a second step, the method provides a second container containing a calcium solution in the concentration ranges described above. When a healthcare medical laboratory professional prepares the liquid thromboplastin reagent for measuring prothrombin time in a patient, the contents of the first and second containers are mixed together and may be used immediately.

The liquid thromboplastin reagent formed according to the method of the invention has a shelf-life of at least 2 years.

In another embodiment of the method of the invention, the first container is the same as described above without a chelator.

In another aspect, the invention is directed to a method for prolonging the shelf-life of a two-part thromboplastin reagent. The method follows the steps provided above for preparing a liquid thromboplastin reagent for measuring prothrombin time in a patient.

BRIEF DESCRIPTION OF THE FIGURES

FIGS. 1A-C show in tables 1-3 that the two component mix and use liquid thromboplastin kit according to the invention is stable for at least a minimum of 24 or more months;

FIG. 3 includes Table 4 comparing chelator-induced stabilization of chelator-treated TF-lipid samples as compared to the untreated TF-lipid controls;

DETAILED DESCRIPTION OF THE INVENTION

Figure 2A:
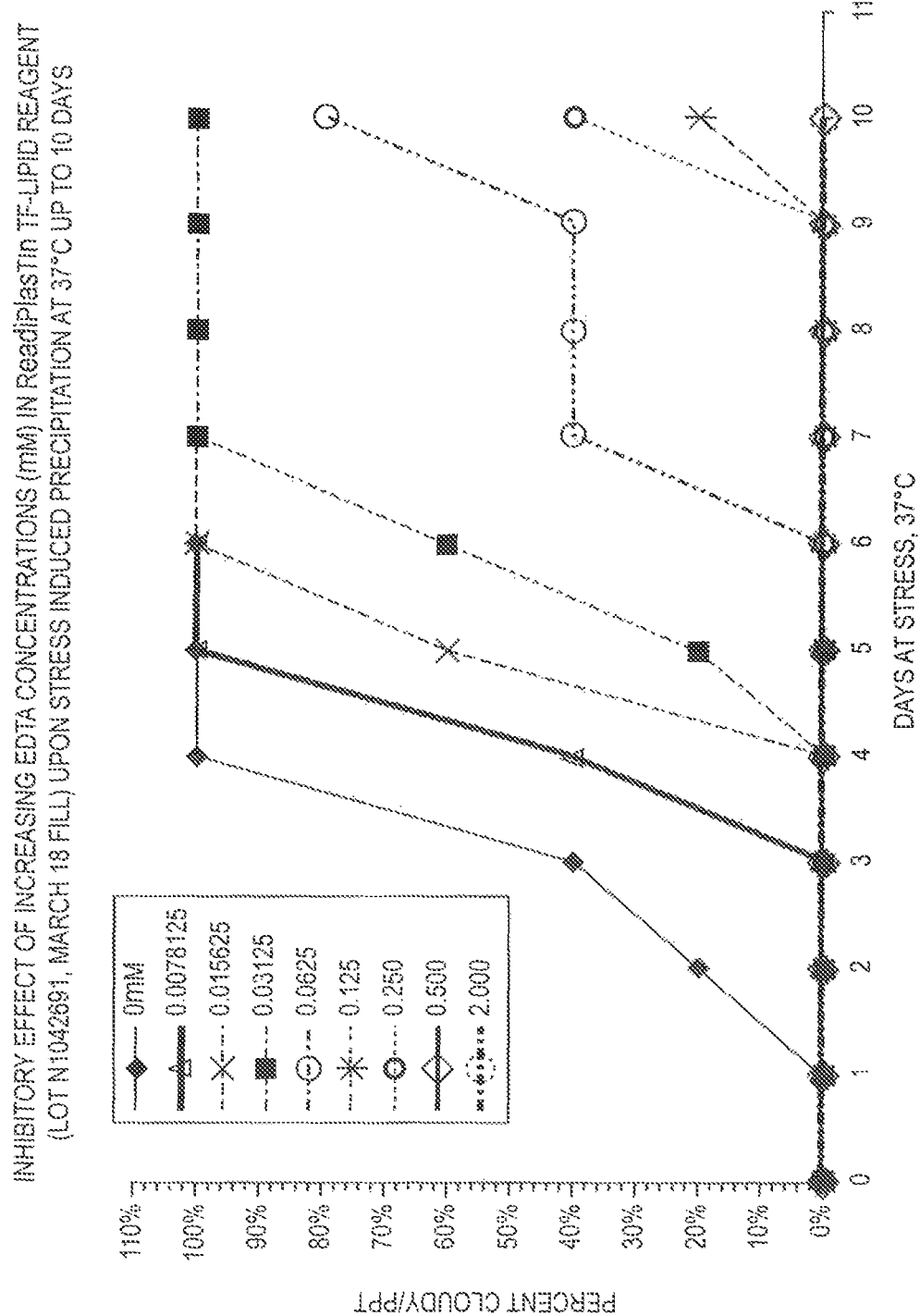
FIGS. 2A and B illustrate chelator-induced protection against precipitation (i.e., instability) in the chelator-treated TF-lipid samples according to the invention.

In one aspect the invention described herein is directed to extending the shelf-life of liquid thromboplastin, a reagent necessary for use in the prothrombin time (PT) assay to test the capacity of a patient's blood to coagulate. In the first embodiment of the invention, a calcium component (e.g., calcium ions in a liquid component with or without buffer) is separate from the tissue factor (TF)-lipid component (e.g., TF-lipid in a liquid component with or without buffer) in a kit for measuring prothrombin time. In this embodiment of the invention, the calcium component is combined with the tissue factor-lipid component just prior to use and when mixed, a working thromboplastin is formed immediately. Thus, according to the invention described herein, the calcium component and the TF-lipid component of the thromboplastin are independent reagents that do not come in contact with one another within the kit until the two components of the kit are mixed together before use. The calcium and TF-lipid components of thromboplastin comprise the two components of the first embodiment of the kit according to the invention.

In this first embodiment of the invention, working liquid thromboplastin is prepared prior to its use in a prothrombin time assay by the user combining the liquid calcium component of the kit with a liquid TF-lipid component of the kit, for example, by mixing 19 volume parts liquid calcium with 1 volume part liquid TF-lipid. Working thromboplastin prepared by mixing the separate calcium and TF-lipid components comprises the first embodiment of "two-part mix (i.e., mixing of the liquid calcium component with the liquid TF-lipid component) and use" (i.e., immediate use of working thromboplastin to measure the PT) configuration of the invention.

The "mix and use" configuration of thromboplastin, as prepared above, is advantageous over prior art liquid thromboplastin because it at least reduces if not prevents divalent metal ion-dependent mechanisms of lipid deterioration, such as divalent metal ion-dependent vesicle fusion leading to precipitation or divalent metal ion-dependent lipid degradation (such as from contaminating lipid-degrading enzymes) which can reduce the performance or stability of the TF-lipid component of the kit. More importantly, because the "mix and use" configuration of the disclosed liquid thromboplastin at least reduces if not prevents the deleterious effects of TF-lipid storage in the presence of divalent metal ions, the two component "mix and use" liquid thromboplastin described herein affords significantly increased shelf life over single component versions presently available, for example, at least up to two years of stability when maintained at 2-8° C.

The two component liquid thromboplastin invention described herein mitigates the effects of stress on the TF-lipid reagent which are caused by but not limited to: thermal stress (e.g., such as improper storage temperature), chemical stress, (e.g., trace contaminants such as phospholipases in the raw material stream used to make the TF-lipid reagent) or mechanical stress (e.g., such as that caused by large scale filtration). These stresses are evident in the kit as precipitation in the TF-lipid component, precipitation in the combined working thromboplastin prepared from the mixture of the TF-lipid and calcium components, or as large changes in the PT of control plasmas versus baseline in the working thromboplastin prepared from the mixture of the TF-lipid and calcium components. In this two component embodiment, the liquid calcium component and the liquid TF-lipid component are independently prepared as separate liquid thromboplastin components, each held in a separate compartment, e.g., separate containers, as discussed below. In separate compartments, the liquid calcium component and liquid TF-lipid components of the embodiment comprise the thromboplastin-to-be prior to assembly by the user to form a working liquid thromboplastin reagent.

In this embodiment of the invention, the separate liquid calcium and TF-lipid components have been engineered to be combined at 19 volume parts calcium component to 1 volume part TF-lipid component so as to achieve a working thromboplastin reagent with the necessary characteristics for suitability in the PT assay. Among the necessary characteristics of the working thromboplastin are component compositions which produce PT results with normal citrated human plasma (i.e., without extrinsic factor deficiencies or VKA or other anticoagulant treatments) in the typical range of about 10-14 seconds (from initiation of coagulation to clot formation). In order to achieve PT results with normal citrated human plasma in this range, working thromboplastins require a calcium concentration sufficient to overwhelm the chelators stabilizing the citrated human patient plasma, typically 0-25 mM and TF-lipid concentrations typically in the range 0-1000 g/L.

In addition, embodiments of this invention described herein (such as 19 volume parts calcium:1 volume part TF-lipid) are also contemplated so as to produce a working thromboplastin with the necessary characteristics that are the same as those described above. An alternate embodiment, for example, includes a kit engineered with 1 volume part of calcium component mixed with 19 volume parts of TF-lipid to make the working thromboplastin. To produce a working thromboplastin with necessary characteristics in the PT assay, such a kit (1 volume part calcium:19 volume parts TF-lipid) would require a much higher calcium concentration in the liquid calcium component and much lower TF-lipid concentration in the TF-lipid component versus the embodiment having 19 volume parts calcium:1 volume part TF-lipid. Both embodiments are contemplated according to the invention since the embodiment employs separation of the calcium and TF-lipid components in the kit and since the working thromboplastin performs equivalently in the PT assay with normal citrated patient plasma.

In yet another (second) embodiment of the invention, one or more chelators are added to the liquid TF-lipid component in millimolar concentrations (e.g., chelators greater than 0 mM to about 100 mM). The one or more chelators protect the liquid TF-lipid component of thromboplastin from divalent metal ion-dependent deterioration. Inclusion of the chelator or a chelating agent in the liquid TF-lipid component of the kit's two components further extends the shelf-life stability of the liquid TF-lipid component by providing protection against divalent metal ion-dependent instability in the TF-lipid component. The extended shelf-life stability of the chelator-treated TF-lipid component further extends the shelf-life stability of the two component "mix and use" liquid thromboplastin beyond two years, for example between 2-5 years or longer, by providing protection against divalent metal ion-dependent instability, induced for example by chemical, mechanical or thermal stress to the TF-lipid component as discussed above.

In this second embodiment, the invention described herein is directed to extending the shelf-life of liquid thromboplastin by separating the calcium component (e.g., calcium ions in a buffered liquid component) from the TF-lipid component in the kit and including a chelator or chelating agent in the separated liquid TF-lipid component to guard against divalent metal ion-dependent deterioration of the lipid. Such divalent metal ion(s) might be present in the TF-lipid component by having been introduced during the manufacturing process as traces in the raw material stream, airborne contaminants such as gypsum, or leaching from apparatus, vessels, or containers in contact with the TF-lipid during manufacture.

A kit according to this second embodiment comprises a first container comprising a tissue factor-lipid component in a buffer with one or more chelators at a concentration ranging between greater than 0 mM to about 100 mM, and a second container comprising a calcium component (e.g. Ca++ ions) in a buffer, for example, a calcium component, at a concentration ranging between about 5 mM to about 500 mM.

In the first embodiment described above where TF-lipid and calcium components are separated but chelator is not present in the TF-lipid, the kit has a shelf-life of at least 1 to 2 years. For example, Tables 1-3 in FIG. 1A-IC show the real time stability data for three distinct lots (FIG. 1A=Lot 1; FIG. 1B=Lot 2 and FIG. 1C=Lot 3) of the two component "mix and use" liquid thromboplastin kit according to the invention when the two component "mix and use" liquid thromboplastin kit was stored at 2-8° C. for a minimum of 24 or more months.

Briefly, to generate the data in FIGS. 1A-C, the two component "mix and use" liquid thromboplastin kits of the first embodiment (without chelators) described above were stored at 2-8° C., removed periodically (e.g., at various monthly time points up to 55 months), and tested for functional performance (Prothrombin Time (PT)(sec)) and fibrinogen (dFib) (mg/dL))) on an ACL TOP® instrument (Instrumentation Laboratory®) in normal control plasma (NC), low abnormal control plasma (Low Ab Con), and high abnormal control plasma (High Abn). Abnormal plasmas used in these studies cause the PT to be prolonged greater than the 10-14 seconds typical for normal control plasmas. The mean values at these times were compared to those values acquired at baseline (0 months). Percent differences at various time points were calculated as follows: % difference:=(Stressed mean−Baseline mean)/(Baseline mean)× 100. Values meeting the specifications in Tables 1 to 3 in FIG. 1 (% difference <10% for the PT of NC; % difference <15% for the PT of Low Ab Con or High Abn; % difference <15% for the dFib of NC, Low Ab Con or High Abn) indicate that the two component "mix and use" liquid thromboplastin kit is stable. Thus, the results summarized from Tables 1 to 3 in FIG. 1 demonstrate that the embodiment described above of the two component "mix and use" liquid thromboplastin kit without chelators is stable for at least a minimum of 24 or more months.

In the second embodiment of the invention in which one or more chelators are added to the two component "mix and use" liquid thromboplastin kit (specifically, a chelator such as EDTA added to the liquid TF-lipid component), the two component "mix and use" liquid thromboplastin kit is stable between 24 (2 years) and 60 months (5 years).

In this second embodiment of the invention, a kit is provided for preparing a liquid thromboplastin reagent for measuring prothrombin time discussed above, the kit comprises a first container comprising tissue factor (TF)-lipid component and a chelator in a buffer. The chelator concentration is greater than about 0 mM to about 100 mM, greater than about 0 to about 50 mM, greater than about 0 mM to about 25 mM, about 10 mM to about 50 mM, for example, and for EDTA, about 0.5 mM and for citrate, about 11 mM, for example. The kit according to this embodiment of the invention further comprises a second container comprising a calcium component (e.g. Ca++ ions), such as, a buffered calcium component, at a concentration ranging between about 5 mM to about 500 mM.

In this second embodiment, the shelf-life of the kit including the contents of the first container and the contents of the second container is between about 2 to 5 years.

Tissue factor for the first and second embodiments directed to a two-part liquid thromboplastin reagent according to the invention described herein can be selected from a recombinant tissue factor or a native tissue factor or a combination of both recombinant and native tissue factor. Tissue factor is also known by other synonyms, such as but not limited to, thromboplastin tissue factor, Factor III, coagulation factor III, CD142, or platelet tissue factor: synonyms for the tissue factor are encompassed within the scope of this invention.

Typically, native tissue factor is extracted from brain or other tissues, such as such as brain, liver, kidney, heart, blood vessels, placenta or endothelial cells, platelets, blood cells (such as, but not limited to, monocytes, neutrophils and other granulocytes), tumor cells, tissue factor-positive micro particles, endothelial cells or sub-endothelial cells (such as, but not limited to, smooth muscle cells or fibroblasts), and egg, soy, plant tissues, yeast, and bacteria.

The concentration of calcium (e.g., a Ca++ ion) in solution for the first and second embodiments directed to a two-part liquid thromboplastin reagent according to the invention described herein ranges from about greater than 0 mM to about 500 mM. For example, the calcium solution is greater than 0 mM to about 90 mM, greater than 0 mM to about 80 mM, greater than 0 mM to about 70 mM, greater than 0 mM to about 60 mM, greater than 0 mM to about 50 mM, greater than 0 mM to about 40 mM, greater than 0 mM to about 30 mM, greater than 0 mM to about 20 mM, greater than 0 mM to about 10 mM, about 5 mM to about 100 mM or about 10 mM to about 30 mM, about 10 mM to about 20 mM, or about 9 mM to about 15.5 mM. The preferred ratio for calcium:TF-lipid is 19:1.

The chelator for the second chelator embodiment directed to a two-part liquid thromboplastin reagent according to the invention described herein is selected from, but not limited to, citrate, ethylenediaminetetraacetic acid (EDTA), ethylene glycol tetraacetic acid (EGTA), nitrilotriacetic acid (NTA), ethylene diamine, N-(2-Acetamido) iminodiacetic acid (ADA), diethylenetriaminepentaacetic acid (DTPA), tartrate, glycinate, BAPTA ((1,2-bis(o-aminophenoxy)ethane-N,N,N',N'-tetraacetic acid), oxalate, phosphate, diphosphate, polyphosphate or organic phosphonates, or combinations of the above.

The concentration of the chelator or the chelating agent (e.g., EDTA) for the second chelator embodiments directed to a two-part liquid thromboplastin reagent according to the invention described herein ranges from about greater than 0 mM to about 100 mM. For example, the chelating agent is in a concentration range of about 0 mM to about 100 mM, greater than about 0 to about 50 mM, greater than about 0 mM to about 25 mM, about 10 mM to about 50 mM, for example, and for EDTA, about 0.5 mM and for citrate, about 11 mM, for example.

The buffer in the tissue factor-lipid component for the first and second embodiments directed to a two-part liquid thromboplastin reagent according to the invention described herein is selected from Tris or any biological buffers or derivatives thereof, including but not limited to, Hepes, MES buffer, Bis-Tris buffer, citrate, ADA buffer, ACES buffer, PIPES buffer, imidazole/imidazolium buffer, Bis-Tris Propane buffer, maleic acid buffer, phosphate buffer, MOPSO buffer, BES buffer, MOPS buffer, TES buffer, DIPSO buffer, MOBS buffer, TAPSO buffer, HEPPSO buffer, POPSO buffer, EPPS (HEPPS) buffer, Tricine buffer, Gly-Gly buffer, Bicine buffer, HEPBS buffer, TAPS buffer, AMPD buffer, TABS buffer, AMPSO buffer, methylmalonate, diethylmalonate, or Glycine Amide hydrochloride buffer.

The calcium component buffer in the calcium component for the first and second embodiments directed to a two-part liquid thromboplastin reagent according to the invention described herein is selected from Tris or any biological buffers or derivatives thereof, including but not limited to, Hepes, MES buffer, Bis-Tris buffer, citrate, ADA buffer, ACES buffer, PIPES buffer, imidazole/imidazolium buffer, Bis-Tris Propane buffer, maleic buffer, phosphate buffer, MOPSO buffer, BES buffer, MOPS buffer, TES buffer, DIPSO buffer, MOBS buffer, TAPSO buffer, HEPPSO buffer, POPSO buffer, EPPS (HEPPS) buffer, Tricine buffer, Gly-Gly buffer, Bicine buffer, HEPBS buffer, TAPS buffer, AMPD buffer, TABS buffer, AMPSO buffer, methylmalonate, diethylmalonate, or Glycine Amide hydrochloride buffer.

The lipid component of the tissue factor-lipid for the first and second embodiments directed to a two-part liquid thromboplastin reagent according to the invention described herein affects functional activity and is made of, but not limited to, a mixture of phospholipids, cholesterol, individual fatty acids, sphingolipids, mono-, di-, or triglycerides or lipid extracts of naturally occurring materials including but not limited to egg, soy or other plant tissues, yeast, bacteria, or animal tissues such as heart, brain, liver, etc.

In another aspect, the invention is directed to a method for preparing a liquid thromboplastin reagent for measuring prothrombin time. The method includes providing a kit comprising a first container, the first container housing a liquid form reagent including tissue factor and a lipid, e.g., a phospholipid, and providing a second container comprising a calcium solution in a buffer (e.g., calcium-buffered component) at a concentration ranging from about 5 mM to about 500 mM in the second container.

In a subsequent step, the liquid form reagent comprising tissue factor and lipids in the first container are mixed with the calcium solution in the second container to form at room temperature the liquid thromboplastin reagent.

The shelf-life of the liquid form thromboplastin reagent without the addition of a chelator is at least about 2 years.

In another aspect, the invention comprises a method for preparing a liquid thromboplastin reagent for measuring prothrombin time. The method comprises providing a kit comprising a first container. The first container comprises a liquid form reagent comprising a tissue factor, a lipid, e.g., a phospholipid mixture, and a chelator (chelator concentration ranges from greater than 0 mM to about 100 mM) and providing a second container comprising a calcium solution in a buffer (e.g., calcium buffered component) at a concentration ranging from about 5 mM to about 500 mM.

In a subsequent step, the liquid form reagent comprising the tissue factor, lipids, and a chelator is mixed with the calcium solution to form at room temperature the liquid thromboplastin reagent.

The shelf-life of the liquid form thromboplastin reagent including a chelator described above is at least greater than 1 year and preferably between 2 to 5 years.

In another aspect, the invention is directed to a method for prolonging the shelf-life of (or stabilizing) a two-part liquid thromboplastin reagent in a kit, comprising providing component (a) comprising a combination of tissue factor and phospholipid in liquid form, providing a chelator (b) and adding the chelator (b) to component (a), providing a component (c) comprising calcium in solution in a concentration range of about 5 mM to about 100 mM to form the prolonged shelf-life two-part liquid thromboplastin reagent having a chelator. The shelf-life of the two-part thromboplastin reagent having a chelator described herein is at least greater than 1 year and at least about 2 years, preferably between 2 and 5 years.

Advantages provided by the invention disclosed herein include but are not limited to:

Providing kits and liquid reagents for a PT assay in which liquid reagents have a greater shelf-life than prior art liquid thromboplastin of at least more than one year and up to at least 5 years.

Providing kits and liquid reagents for a PT assay in which reagents are protected against stress-induced (e.g., contaminant-induced mechanical, chemical, or thermal-induced stress) instability of reagents useful in determining prothrombin time.

Simplifying and minimizing reagent preparation time for a PT assay.

EXAMPLES OF THE VARIOUS EMBODIMENTS OF THE INVENTION

The two component mix and use liquid thromboplastin according to the invention described herein includes calcium ions (Ca++) in a component separate from the liquid tissue factor-lipid portion (native or recombinant TF-lipid), and the working thromboplastin was prepared prior to use by dilution of the native or recombinant TF-lipid in a buffer (e.g., calcium buffered component). This "mix and use" configuration is unique in the marketplace for liquid thromboplastins, and keeps deleterious lipid degrading mechanisms such as calcium-dependent vesicle fusion or metal ion-dependent lipid degradation from affecting the susceptible lipids. In addition, to further protect against metal ion vesicle fusion leading to thromboplastin instability and precipitation, chelators such as EDTA and citrate may be introduced into the TF-lipid portion to inhibit this metal ion induced mechanism. The presence of the modest (i.e., millimolar) chelator levels in the reagent portion is made irrelevant in the working thromboplastin because mixing with the excess of calcium in the component overrides the chelator levels in the final working thromboplastin). This protective mechanism using chelators is not possible in prior art single component thromboplastin since chelator concentrations in a single component thromboplastin are required within the working thromboplastin to be in excess to overwhelm the citrate chelator in human plasma, and therefore any and all chelators added to the TF-lipid component would necessarily be overwhelmed by calcium levels needed to activate coagulation. Moreover, the "mix and use" configuration of the liquid thromboplastin described herein minimizes reagent preparation time needed for to a ready-to-use thromboplastin reagent, where practically no incubation time is required before use of the thromboplastin reagent. This is a distinction from prior art thromboplastin reagents and is more user-friendly and efficient than prior art thromboplastin reagents.

Figure 2B:
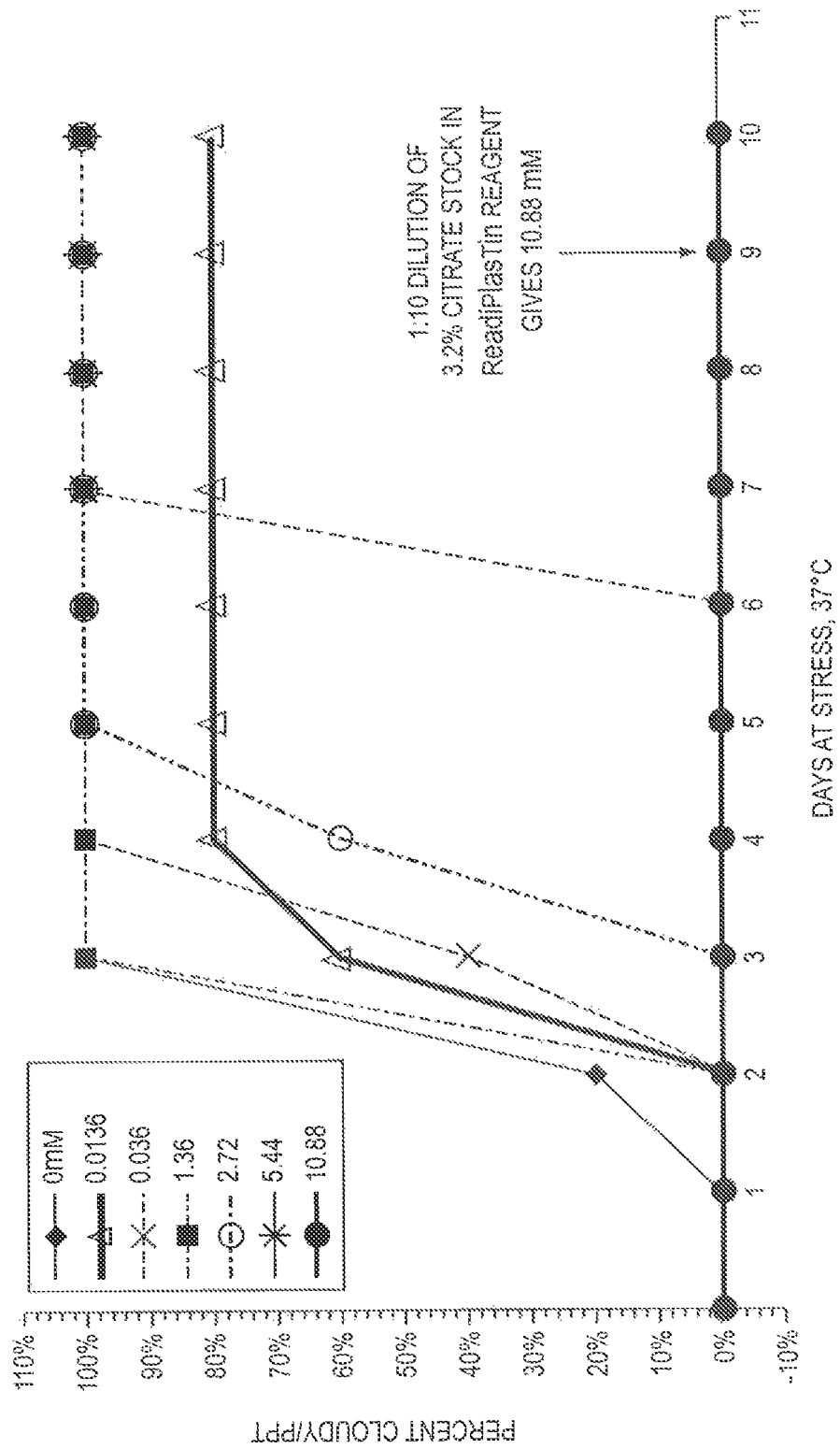

During the development of the two component mix and use liquid thromboplastin, some sources of instability in the TF-lipid portion were identified. Varying levels of trace phospholipase activities (e.g., of phospholipases D, A1, A2 and C), phospholipase D activity in particular, were detected in the degraded TF-lipid component of aged kits. The phospholipase D activity could be demonstrated as originating in the rTF raw material, and these were minimized in the raw material stream using a pre-qualification assay for phospholipase D. Also, mechanical stress (such as from cartridge filtration) caused a temporary instability visible during thermal stress (37° C.), which resolved itself within four months of storage at 2-8° C. This instability was accompanied by an increase in the population of cloudy TF-lipid reagent vials with time at 37° C. The effects of both these issues were mitigated by using mM (e.g., greater than 0 mM to about 100 mM) levels of chelator in the TF-lipid reagent vials. As illustrated in FIGS. 2A and 2B, inclusion of a minimum of 0.5 mM EDTA (FIG. 2A) or 10.88 mM sodium citrate (FIG. 2B) completely eliminated the instability induced in ReadiPlasTin®, a PT reagent, (Instrumentation Laboratory Company, Bedford, Mass.) by the large scale filtration process in a dose-dependent manner.

Figure 4:
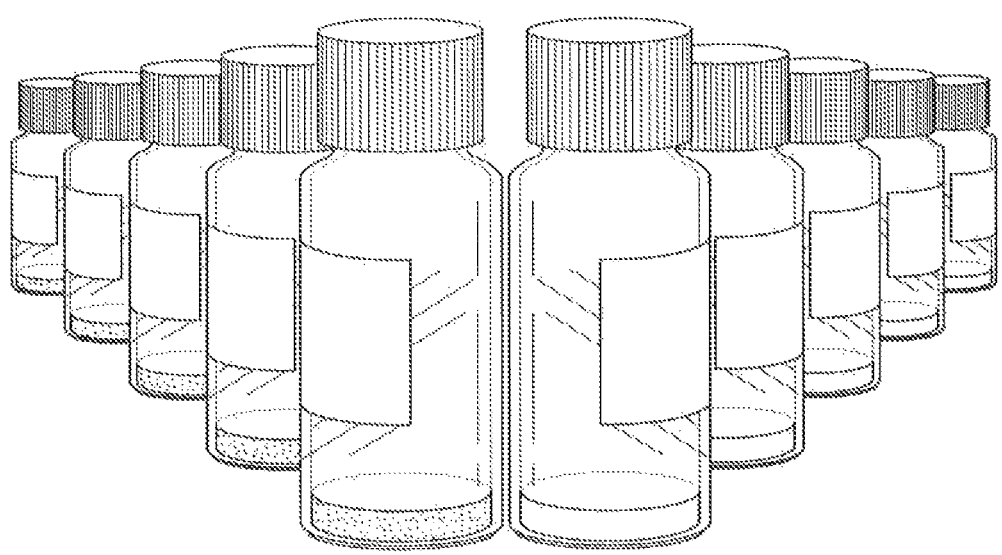
FIG. 4 illustrates untreated (cloudy) samples in the bottom of the left hand vials and chelator-treated (clear) samples in the bottom of the right hand vials; the data disclosed in FIG. 3 corresponds to the left hand (untreated) and right hand (chelator-treated) vials.

Furthermore, referring to Table 4 in FIG. 3, the chelator presence also provided a significant level of functional protection against prolongation of the PT. Table 4 compares material filtered through a 10-inch 0.2 micron spiral cartridge filter during production of the TF-lipid component for a manufactured lot "P4" (Lot N1042691: 19 parts calcium, 1 part TF-lipid, same concentrations (typically 9-15.5 mM calcium in the diluent, with TF-lipid containing 3 g/L lipid and 3.375 to 4.5 mg/L TF) which was treated with EDTA (upper table in FIG. 3) and untreated with EDTA (lower table in FIG. 3) prior to stress at 37° C. for 10 days. After dilution with the matching calcium component (1 part TF-lipid, 19 parts calcium component) to make working thromboplastin, the EDTA containing samples showed significant protection against filtration induced susceptibility to stress, and gave prothrombin times for control materials as expected for unstressed two component mix and use liquid thromboplastin. Thus, FIGS. 3 and 4 exemplify that a chelator (e.g., EDTA) stabilized the chelator-treated samples (e.g., the TF-lipid portion) and produced a robust stability as compared to the untreated samples. Most samples without chelator demonstrated precipitation and failed the test. FIG. 4 illustrates the cloudy (precipitation) samples in the bottom of the left hand vials which were untreated with chelator (left hand vials), and the clear samples (no precipitation) in the bottom of the right hand vials treated with a chelator.

FIG. 5 illustrates the protection chelators afford the TF-lipid portion of ReadiPlasTin from contaminating phospholipase (PLase) introduced into freshly prepared reagent (TF-lipid lot N1065947). Fractions containing phospholipase D activity, detected as free choline from degradation of phosphatidylcholine (Thermo Fisher, Amplex Red kit #A12219), were isolated from Sf9 insect cell extracts, which is the same source material for the TF used in making ReadiPlasTin. The PLase-containing fractions were identified and isolated in the Superdex 200 gel filtration elution profile (fractions 14-16, GE Healthcare Bio-Sciences, Pittsburgh, Pa. 15264-3065) distinct from TF fractions (fractions 6-12), combined and concentrated in a stirred cell concentrator over a YM-10 (EMD Millipore Headquarters Billerica, Mass. 01821) diafiltration membrane by approximately 200-fold (~0.5 mg/mL), stabilized to 5 mM calcium using a 5-fold concentrated ("5×") Amplex Red choline assay buffer at 25 mM calcium (4 volumes concentrate+1 volume "5×", then diluted eight times at 1:10 each using "5×" Amplex Red choline assay buffer diluted to 5 mM calcium). The resulting series of 10-fold diluted stocks with PLase D activity were added to 1% of volume (10 µL into 1.0 mL TF-lipid component) to adulterate the TF-lipid portion of ReadiPlasTin N1065947 vials which were pre-treated with or without 1.0 mM EDTA chelator. After acceleration of the test by stressing 10 days at 37° C., each of the vials was assayed for choline using a sensitive Amplex Red PLase-D fluorescence assay (kit #A12219; Thermo Fisher Scientific Headquarters, MA 02451) to detect whether phosphatidylcholine in the TF-lipid component of the formulation had degraded to free choline.

Figure 5A:
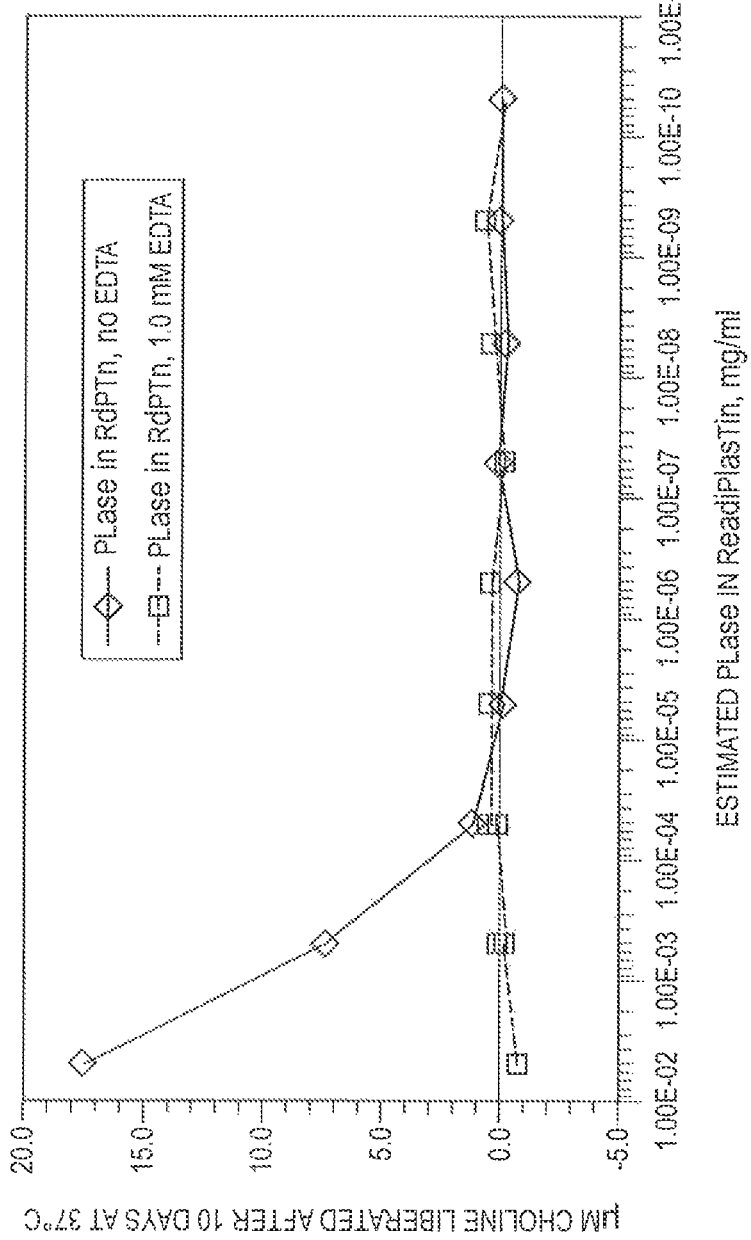
FIG. 5A illustrates (PLase)-induced lipid degradation of phosphatidylcholine under accelerating conditions (37° C. for 10 days) with or without EDTA chelator.
Figure 5B:
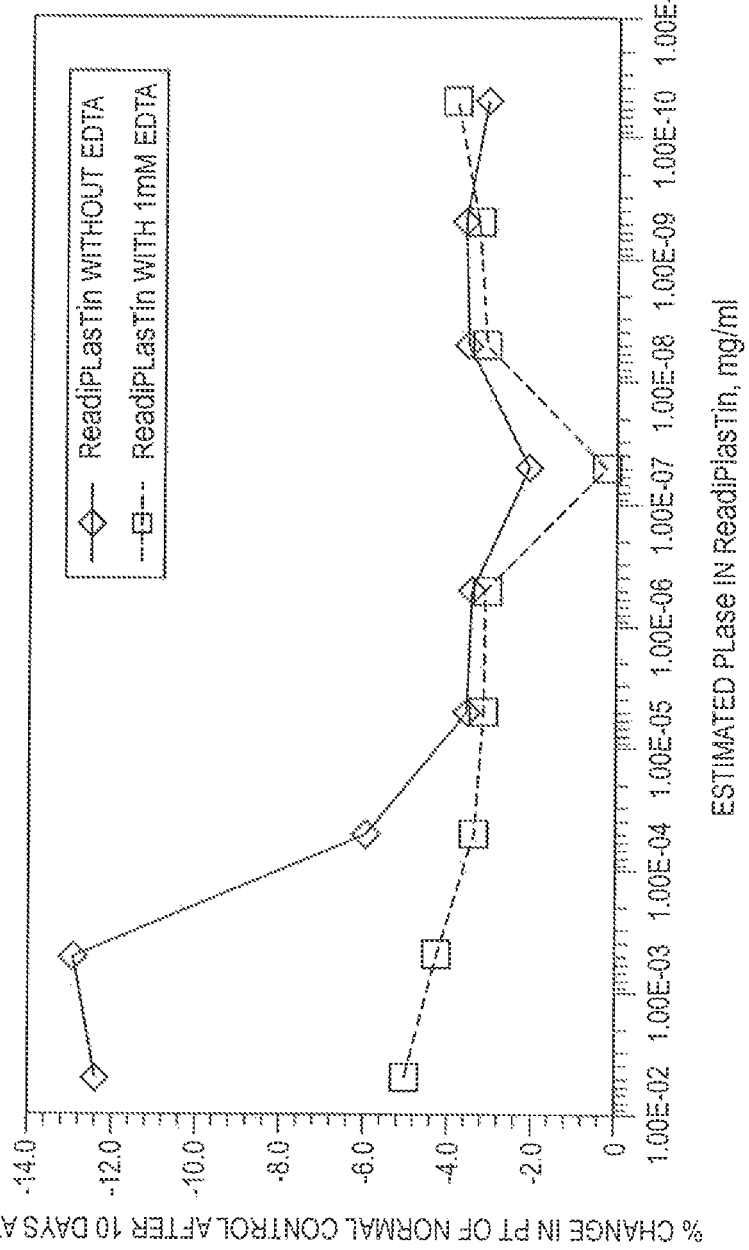
FIG. 5B illustrates the percent change in PT in normal control plasma due to phosphatidylcholine degradation in ReadiPlasTin® with and without chelator. Without chelator treatment, degraded phosphatidylcholine is exhibited as free choline above baseline at the highest PLase concentrations; while with chelator treatment, levels of choline detected are at baseline over all concentrations of spiked PLase/calcium in the TF-lipid.

In the series where the TF-lipid component was untreated with chelator (FIG. 5A), choline was detected above baseline (i.e., at 1-18 µM) in the vials where the PLase was highest (5E-3 to 5E-5; i.e., 5×10-3 to 5×10-5) mg/mL, diamonds, FIG. 5A), but was undetectable (i.e., near 0 µM) in vials treated with the chelator (squares, FIG. 5A). Similar protection for the TF-lipid component treated with chelator versus untreated TF-lipid component was found for working thromboplastins prepared from these samples (FIG. 5B). Measurements of % difference from baseline for the PT of Normal Control Plasma for the TF-lipid series treated with chelator (1 mM EDTA, squares, FIG. 5B) were low and constant across all concentrations of PLase D contaminant (between −0% to −5%). Measurements of the % difference from baseline for the PT of Normal Control Plasma for the untreated (without EDTA) TF-lipid series (diamonds, FIG. 5) were higher across the range of PLase D contaminant (−2% to −13%). And at the highest levels exceeded specification for allowable PT % difference (<10% for Normal Control). The results illustrated in FIG. 5 provide evidence that use of chelator in the TF-lipid portion of ReadiPlasTin protects against phosphatidylcholine phospholipid degradation caused by PLase contaminant under accelerating (e.g. thermally stressing) conditions.

While the present invention has been described in terms of certain exemplary embodiments, it will be readily understood and appreciated by one of ordinary skill in the art that it is not so limited, and that many additions, deletions, and modifications to the preferred embodiments may be made within the scope of the invention as hereinafter claimed.

What is claimed is:

1. A system comprising:
   a first compartment containing a coagulation Factor III in a buffer combined with a lipid mixture and a chelator, wherein the chelator comprises at least one of: citrate, Ethylenediaminetetraacetic acid (EDTA), Ethylene glycol-bis(β-aminoethyl ether)-N,N,N',N'-tetraacetic acid (EGTA) in a liquid form, Nitrilotriacetic acid (NTA), ethylene diamine, N-(2-Acetamido)iminodiacetic acid (ADA), diethylenetriaminepentaacetic acid (DTPA), 1,2-bis(o-aminophenoxy)ethane-N,N,N',N'-tetraacetic acid (BAPTA), oxalate, triphosphate, diphosphate, polyphosphate, or organic phosphonates, and wherein the chelator has a concentration that is within a range of greater than 0 millimolar (mM) to 100 mM; and
   a second compartment containing a calcium component in a buffer at a concentration ranging from about 5 mM to about 500 mM, wherein the concentration of the calcium component in the second compartment is in excess of the concentration of the chelator in the first compartment, and wherein the concentration of the calcium component is sufficient, upon mixing of contents of the first compartment with contents of the second compartment, to overwhelm the concentration of the chelator at least to an extent that sufficient free calcium is available to activate coagulation in a blood sample.

2. The system of claim 1, wherein the system has a shelf-life of at least 2 years.

3. The system of claim 1, wherein the lipid mixture comprises at least one of a recombinant tissue factor or a native tissue factor.

4. The system of claim 3, wherein the native tissue factor is an extraction from at least one of a brain, a liver, a kidney, a heart, blood vessels, a placenta or endothelial cells, platelets, blood cells, tumor cells, tissue factor-positive micro particles, endothelial cells or sub-endothelial cells and egg, soy, plant tissues, yeast, or bacteria.

5. The system of claim 3, wherein the native tissue factor comprises an extraction from animal tissue.

6. The system of claim 1, wherein the lipid mixture comprises an extraction from animal tissue.

7. The system of claim 1, wherein the concentration of the calcium component is in a range of 9 mM to 15.5 mM.

8. The system of claim 1, wherein the concentration of the chelator is in a range of 0.5 mM to 11 mM.

9. The system of claim 1, wherein the lipid mixture comprises at least one of phospholipids, cholesterol, fatty acids, sphingolipids, mono-glycerides, di-glycerides, tri-glycerides, or lipid extracts of naturally occurring materials.

10. The system of claim 9, wherein the lipid extracts of naturally occurring materials comprise at least one of egg, soy, plant tissues, yeast, bacteria, or animal tissues.

11. The system of claim 1, wherein the system comprises a kit.

12. The system of claim 1, wherein the first compartment comprises a first container and the second compartment comprises a second container.

13. A system comprising:
a first compartment containing a thromboplastin tissue factor in a buffer combined with a lipid in a liquid form and a chelator, wherein the chelator comprises at least one of: citrate, Ethylenediaminetetraacetic acid (EDTA), Ethylene glycol-bis(β-aminoethyl ether)-N,N,N',N'-tetraacetic acid (EGTA) in a liquid form, Nitrilotriacetic acid (NTA), ethylene diamine, N-(2-Acetamido)iminodiacetic acid (ADA), diethylenetriaminepentaacetic acid (DTPA), 1,2-bis(o-aminophenoxy)ethane-N,N,N',N'-tetraacetic acid (BAPTA), oxalate, triphosphate, diphosphate, polyphosphate, or organic phosphonates, and wherein the chelator has a concentration that is within a range of greater than 0 millimolar (mM) to 100 mM; and
a second compartment containing a calcium component in a buffer at a concentration ranging from about 5 mM to about 500 mM, wherein the concentration of the calcium component in the second compartment is in excess of the concentration of the chelator in the first compartment, and wherein the concentration of the calcium component is sufficient, upon mixing of contents of the first compartment with contents of the second compartment, to overwhelm the concentration of the chelator at least to an extent that sufficient free calcium is available to activate coagulation in a blood sample.

14. The system of claim 13, wherein the lipid comprises at least one of phospholipids, cholesterol, fatty acids, sphingolipids, mono-glycerides, di-glycerides, tri-glycerides, or lipid extracts of naturally occurring materials.

15. The system of claim 14, wherein the lipid comprises an extract of naturally occurring materials comprising at least one of egg, soy, plant tissues, yeast, bacteria, or animal tissues.

16. The system of claim 13, wherein the thromboplastin tissue factor is extracted from animal tissue.

17. The system of claim 13, wherein the system is a kit.

18. The system of claim 13, wherein the first compartment comprises a first container and the second compartment comprises a second container.

19. A method comprising:
at room temperature, mixing content of a first compartment containing a liquid form reagent with content of a second compartment containing a calcium solution to form a liquid thromboplastin reagent at room temperature;
wherein the liquid form reagent comprises a thromboplastin tissue factor in a first buffer, a lipid mixture, and a chelator comprising at least one of: citrate, Ethylenediaminetetraacetic acid (EDTA), Ethylene glycol-bis(β-aminoethyl ether)-N,N,N',N'-tetraacetic acid (EGTA) in a liquid form, Nitrilotriacetic acid (NTA), ethylene diamine, N-(2-Acetamido)iminodiacetic acid (ADA), diethylenetriaminepentaacetic acid (DTPA), 1,2-bis(o-aminophenoxy)ethane-N,N,N',N'-tetraacetic acid (BAPTA), oxalate; triphosphate, diphosphate, polyphosphate, or organic phosphonates, and wherein the chelator has a concentration that is within a range of about 0 millimolar (mM) to about 100 mM; and
wherein the content of the second compartment comprises a calcium component in a second buffer at a concentration range of about 5 mM to about 500 mM, wherein a concentration of the calcium component is in excess of the concentration of the chelator, and wherein the concentration of the calcium component is sufficient, upon the mixing of the content of the first compartment with the content of the second compartment, to overwhelm the concentration of the chelator at least to an extent that sufficient free calcium is available to activate coagulation in a blood sample.

20. The method of claim 19, wherein the liquid thromboplastin reagent has a shelf-life of at least 2 years.

21. The method of claim 19, wherein the thromboplastin tissue factor comprises at least one of a recombinant tissue factor and phospholipids, cholesterol, fatty acids, sphingolipids, mono-glycerides, di-glycerides, tri-glycerides, or lipid extracts of naturally occurring materials.

22. The method of claim 21, wherein the lipid extracts of naturally occurring materials comprise at least one of egg, soy, plant tissues, yeast, bacteria, or animal tissues.

23. The method of claim 19, wherein the thromboplastin tissue factor is an extraction from animal tissue.

24. The method of claim 19, wherein the first buffer or the second buffer comprises at least one of a Hepes, a MES buffer, a Bis-Tris buffer, citrate, an ADA buffer, an ACES buffer, a PIPES buffer, an imidazole/imidazolium buffer, a Bis-Tris Propane buffer, a maleic acid buffer, a phosphate buffer, a MOPSO buffer, a BES buffer, a MOPS buffer, a TES buffer, a DIPSO buffer, a MOBS buffer, a TAPSO buffer, a HEPPSO buffer, a POPSO buffer, an EPPS (HEPPS) buffer, a Tricine buffer, a Gly-Gly buffer, a Bicine buffer, a HEPBS buffer, a TAPS buffer, an AMPD buffer, a TABS buffer, an AMPSO buffer, methyl malonate, diethylmalonate, or a Glycine Amide hydrochloride buffer.

25. The method of claim 19, wherein the first compartment comprises a first container and the second compartment comprises a second container.

26. The method of claim 19, wherein the lipid mixture comprises at least one of phospholipids, cholesterol, fatty acids, sphingolipids, mono-glycerides, di-glycerides, tri-glycerides, or lipid extracts of naturally occurring materials.

27. The system of claim 4, wherein the lipid mixture comprises at least one of phospholipids, cholesterol, fatty acids, sphingolipids, mono-glycerides, di-glycerides, tri-glycerides, or lipid extracts of naturally occurring materials.

28. The system of claim 13, wherein the thromboplastin tissue factor comprises at least one of a recombinant tissue factor and phospholipids, cholesterol, fatty acids, sphingolipids, mono-glycerides, di-glycerides, tri-glycerides, or lipid extracts of naturally occurring materials.

* * * * *